United States Patent [19]

Johnson

[11] Patent Number: 5,082,989
[45] Date of Patent: Jan. 21, 1992

[54] INTEGRATED PROCESS FOR $C_4$, $C_5$ AND $C_6$ ISOMERIZATION

[75] Inventor: Brian H. Johnson, Arlington Heights, Ill.

[73] Assignee: UOP, Des Plaines, Ill.

[21] Appl. No.: 459,160

[22] Filed: Dec. 29, 1989

[51] Int. Cl.$^5$ ............................................. C07C 5/13
[52] U.S. Cl. ..................................... 585/748; 585/751
[58] Field of Search ................................. 585/748, 751

[56] References Cited

U.S. PATENT DOCUMENTS

| | | |
|---|---|---|
| 2,939,896 | 6/1960 | Myers et al. . |
| 3,242,228 | 3/1966 | Riordan et al. . |
| 3,789,082 | 1/1974 | Cook et al. . |
| 4,113,789 | 9/1978 | Rao et al. . |
| 4,804,803 | 2/1989 | Schmidt et al. . |
| 4,877,919 | 10/1989 | Schmidt ............................ 585/748 |

Primary Examiner—Helen M. S. Sneed
Assistant Examiner—James Saba

[57] ABSTRACT

A process is disclosed for the isomerization of a $C_4$ feedstock and a $C_5$-$C_6$ feedstock that reduces equipment and operating expenses by utilizing a process flow scheme that provides beneficial heat integration and facilitates the use of a common recovery zone while permitting a wide variation in the relative ratio of a $C_4$ to a $C_5$-$C_6$ feedstock. The isomerization of the $C_4$ feedstock takes place in a separate reaction zone. The effluent from the $C_4$ isomerization zone is heat exchanged against or mixed with the $C_5$-$C_6$ feedstock ahead of an additional isomerization zone that converts the $C_5$-$C_6$ hydrocarbons, and if present, normal $C_4$ hydrocarbons, to more highly branched hydrocarbons. Effluents from both isomerization zones enter a common separation section that removes light gases from the isomerate product.

This invention simplifies the simultaneous isomerization of $C_4$ and $C_5$-$C_6$ feedstocks. If offers significant cost and operational advantages to newly designed units and is beneficial in the revamp of existing isomerization units to either add or improve butane isomerization capabilities. For example, butane isomerization capability may be incorporated into an existing $C_5$-$C_6$ isomerization unit by adding as few pieces of major equipment as a butane drier, a feed exchanger, and one or two reactors.

13 Claims, 2 Drawing Sheets

Figure 2

INTEGRATED PROCESS FOR $C_4$, $C_5$ AND $C_6$ ISOMERIZATION

BACKGROUND OF THE INVENTION

This invention relates generally to the isomerization of hydrocarbons. This invention relates more specifically to the isomerization of $C_4$, $C_5$ and $C_6$ cyclic hydrocarbons using a solid catalyst.

DESCRIPTION OF THE PRIOR ART

High octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to achieve high octane ratings. Catalytic reforming and catalytic isomerization are two widely used processes for this upgrading.

A gasoline blending pool normally included $C_4$ and heavier hydrocarbons having boiling points of less than 205° C. (400° F.) at atmospheric pressure. This range of hydrocarbon includes $C_4$–$C_6$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement can also be obtained by using isomerization to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Therefore, it is common practice to charge the $C_6$ paraffins to an isomerization unit to obtain $C_6$ isoparaffin hydrocarbons. Consequently, octane upgrading commonly uses isomerization to convert $C_6$ and lighter boiling hydrocarbons and reforming to convert $C_7$ and higher boiling hydrocarbons.

The isomerization of paraffins is a reversible first order reaction. The reaction is limited by thermodynamic equilibrium. It has been generally found that lower temperatures shift the equilibrium of $C_5$ and $C_6$ hydrocarbons toward higher isoparaffin to normal paraffin ratios. These temperatures are typically in the range of 105°–180° C. (200°–355° F.). When isomerizing butane, its refractory nature demands somewhat higher temperatures usually greater than 170° C. (340° F.) to obtain high equilibrium ratios of isobutane to butane.

A number of catalyst systems have been used in effecting isomerization reactions. Traditional catalyst systems are a hydrochloric acid promoted aluminum chloride system and a supported aluminum chloride catalyst. Recently zeolite catalysts, particularly mordenite, are also finding increased usage due to their decreased sensitivity to sulfur and water. A platinum group metal is usually incorporated into both catalysts. All of these catalyst systems are very reactive and can generate undesirable side reactions such as disproportionation and cracking. These side reactions not only decrease the product yield but can form olefinic fragments that combine with the catalyst and shorten its life. One commonly practiced method of controlling these undesired reactions has been to carry out the reaction in the presence of hydrogen. However, high concentrations of hydrogen and high molecular weight species tend to inhibit the butane isomerization reactions. Therefore, it has been difficult to isomerize butane in the presence of $C_5$–$C_6$ hydrocarbons without sacrificing isobutane yields or obtaining low yields of $C_4$–$C_6$ isoparaffins along with undesirable high gas production and catalyst fouling.

As a result butane isomerization and the isomerization of $C_5$ and $C_6$ hydrocarbons are typically carried out in separate reaction zones and processes. The use of separate processes increases the equipment and operating expenses associated with the isomerizing of $C_4$ through $C_6$ hydrocarbons.

INFORMATION DISCLOSURE

U.S. Pat. No. 2,939,896 issued to Myers discloses a catalyst for the isomerization of $C_4$–$C_6$ hydrocarbons consisting of an activated alumina with 0.01 to 5 wt. % platinum, 0.05 to 8 wt. % chlorine, and at least 0.2 wt. % of a sulfide ion. The catalyst is used in an isomerization process at temperatures in the range of from 320°–490° C. (610°–915° F.).

U.S. Pat. No. 3,242,228 issued to Riordan et al. teaches an isomerization catalyst consisting of an alumina base with 0.01 to 1.0 wt. % platinum, and 2.5 to 7.0 wt. % chlorine. The catalyst is used at process conditions including a liquid hourly space velocity (LHSV) of from 0.5 to 2.0, a hydrogen to hydrocarbon mole ratio within the range of from 0.1:1 to 5.0:1, and a temperature of 150°–200° C. (300°–390° F.) for butane isomerization, or a temperature of 120°–160° C. (250°–320° F.) for $C_5$–$C_6$ isomerization.

U.S. Pat. No. 3,789,082 to Cook et al. is directed to a method for practicing low temperature isomerization using a chloride platinum-alumina catalyst. The process operates in the presence of a hydrogen chloride promoter in an amount up to 0.1 to 5 wt. % of the feed stock and temperatures in the range of 100°–200° C. (210°–390° F.) for the isomerization of feedstreams comprising $C_4$ and/or $C_5$ and/or $C_6$ fractions.

U.S. Pat. No. 4,113,789 issued to Rao et al. mentions the isomerization of $C_4$–$C_6$ hydrocarbons at temperatures ranging from 120°–180° C. (250°–355° F.) and butane at temperatures ranging from 150°–200° C. (300°–390° F.) in the presence of a chlorided platinum alumina catalyst and hydrogen to hydrocarbon ratios in the range of 0.1:1.0 to 1:1.

U.S. Pat. No. 4,804,803 discloses a process for the isomerization of $C_4$–$C_6$ paraffins that uses a highly active chlorided, platinum alumina catalyst to carry out the process with a hydrogen to hydrocarbon ratio of 0.05 or less in the effluent from the isomerization zone.

BRIEF DESCRIPTION OF THE INVENTION

This invention is a process for the isomerization of a $C_4$ feedstock and a $C_5$–$C_6$ feedstock that reduces equipment and operating expenses by utilizing a process flow scheme that provides beneficial heat integration and facilitates the use of common recovery zone while permitting a wide variation in the relative ratio of the $C_4$ to the $C_5$–$C_6$ feedstock. The isomerization of the $C_4$ feedstock takes place in a separate reaction zone. The effluent from the $C_4$ isomerization zone is heat exchanged against or mixed with the $C_5-C_6$ feedstock ahead of an additional isomerization zone that converts the $C_5-C_6$ hydrocarbons, and if present normal $C_4$ hydrocarbons, to more highly branched hydrocarbons. Effluents from both isomerization zones enter a common separation section that removes light gases from the isomerate product.

Accordingly in one embodiment, this invention is a process for isomerizing a first feedstock comprising normal butane and a second feedstock comprising $C_5$ and $C_6$ paraffinic hydrocarbons. The process combines the first feedstock with at least a first portion of a hydrogen stream to produce a first combined feedstream comprising hydrogen and normal butane. The first combined feedstream is passed to a first isomerization zone and contacted, at butane isomerization conditions, with an isomerization catalyst. A first isomerization zone effluent comprising isobutane and hydrogen is withdrawn from said first isomerization zone. The first isomerization zone effluent at least indirectly contacts the second feedstock which is admixed with at least a portion of the hydrogen from the hydrogen stream to produce a second combined feedstream. The second combined feedstream passes to a second isomerization zone and contacts isomerization catalyst at conditions for the isomerization of $C_5$ and $C_6$ hydrocarbons. A second isomerate effluent is withdrawn from the second isomerization zone and passed along with the first effluent to a common separation zone. A light gas stream containing hydrogen and at least one product stream comprising branched-chain hydrocarbons are withdrawn from said separation zone.

In a more kimited embodiment, this invention comprises a process for isomerizing a first feedstock comprising normal butane and a second feedstock comprising $C_5$ and $C_6$ paraffinic hydrocarbons. The process includes the steps of combining the first feedstock with at least a portion of a hydrogen stream to produce a first combined feedstream comprising hydrogen and normal butane; passing the first combined feedstream to the first isomerization zone and contacting the first combined feedstream, at butane isomerization conditions, with an isomerization catalyst comprising alumina, 0.01 to 0.25 wt. % platinum and from 2-10 wt. % of a chloride component and withdrawing the first isomerization zone effluent comprising isobutane and hydrogen; mixing at least a portion of the first isomerization zone effluent with the second feedstock to produce a second combined feedstream and maintaining a hydrogen concentration in the second combined feedstream that will produce a hydrogen to hydrocarbon ratio in a second effluent stream from a second isomerization zone that is less than 0.1; passing the second combined feedstream to the second isomerization zone and contacting the second combined feedstream with an isomerization catalyst comprising alumina, 0.01 to 0.25 wt, % platinum and from 2-10 wt. % of a chloride component at conditions for the isomerzation of $C_5$ and $C_6$ hydrocarbons, the conditions including a temperature that is lower than the temperature in the first isomerization zone, and withdrawing a second isomerization zone effluent having said hydrogen to hydrocarbon ratio of less than 0.1 from the second isomerization zone; passing the first and second effluent stream to a separation zone; withdrawing a first light gas stream, containing essentially all of the hydrogen entering the separation zone from the separation zone and removing the light gas stream from the process; and withdrawing at least one product stream comprising branched-chain hydrocarbons from the separation zone.

Additional details, objects and embodiments of this invention are disclosed in the following detailed description of this invention.

BRIEF DESCRIPTION OF THE DRAWINGS

FIG. 2 is schematic diagram of an isomerization zone arranged in accordance with this invention showing the direct mixing of the first effluent with the second feedstock and the mixing of a portion of the hydrogen stream with the second feedstock.

DETAILED DESCRIPTION OF THE INVENTION

Figure 1:
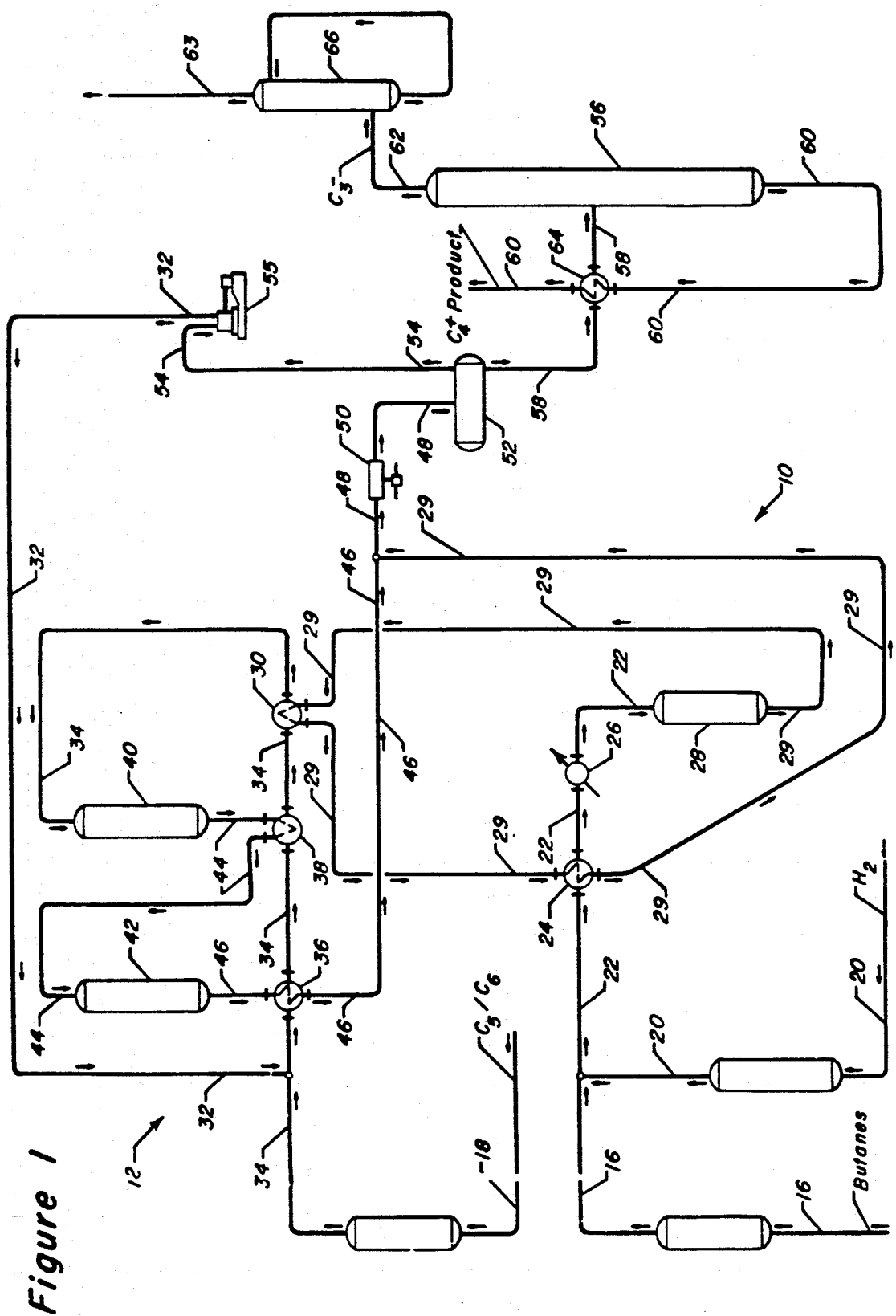
FIG. 1 is a schematic diagram of an isomerization process arranged in accordance with this invention showing indirect contact of the first effluent with the second feedstock and the recycle of hydrogen from the separation section.

This invention simplifies the simultaneous isomerization of $C_4$ and $C_5-C_6$ feedstocks. It offers significant cost and operational advantages to newly designed units and is beneficial in the revamp of existing isomerization units to either add or improve butane isomerization capabilities. For example, butane isomerization capability may be incorporated into an existing $C_5-C_6$ isomerization unit by adding as few pieces of major equipment as a butane drier, a feed exchanger, and one reactor. Moreover, this invention can be incorporated into a new or existing isomerization unit in a variety of arrangements.

FIG. 1 provides a simplified flow diagram of one arrangement for the process of this invention. In order to facilitate an understanding of this invention, additional equipment such as valves, pumps and instruments have been omitted from FIG. 1.

As FIG. 1 shows, the process of this invention uses a $C_4$ isomerization zone 10, a $C_5-C_6$ isomerization zone 12, and a common separation facilities 14. This process uses two feedstreams, a first feedstock that enters an isomerization zone operated for $C_4$ isomerization and a second feedstock that enters an described. From charge heater 30, line 34 delivers the second combined feedstream to reactor 40. Reactor 40 contacts the feedstream with the catalyst contained therein to produce an intermediate isomerate product made up primarily of isopentanes and isohexanes. Line 44 conveys the isomerate product through exchanger 38 and into reactor 42. Contact with the catalyst in reactor 42 further isomerizes the intermediate isomerate product stream to produce a $C_5-C_6$ isomerate product. The $C_5-C_6$ isomerate product is withdrawn from reactor 42 by a line 46 which directs the $C_5-C_6$ isomerate product through exchanger 36 and into admixture with the $C_4$ isomerate product carried by line 29 to produce a single isomerate product from the two feedstocks that first entered the process.

The feedstocks that can be used in this invention include hydrocarbon fractions rich in $C_4$ normal paraffins and hydrocarbon fractions rich in $C_5-C_6$ normal paraffins. The term "rich" is defined to mean a stream having more than 50% of the mentioned component. A suitable feedstream for the $C_4$ isomerization zone will have at least 40 mol % normal butane with at least 25% of any balance comprising isobutane. Preferred feedstocks are substantially pure normal paraffin streams having over 60 mol % normal butane. Suitable $C_4$ feedstreams are available from several sources in a refinery or as field butane streams.

The feedstream for the $C_5$–$C_6$ isomerization zone will contain large quantities of normal and mono-methyl branched paraffins. Preferred feedstock are substantially pure normal hydrocarbons of roughly equal proportions of $C_5$ and $C_6$ paraffins. Other useful feedstocks include light natural gasoline, light straight run naphtha, gas oil condensate, light raffinates, light reformate, light hydrocarbons, and straight run distillates having distillation end points of about 77° C. (170° F.) and containing substantial quantities of $C_5$ and $C_6$ paraffins. The isomerization zone operated for $C_5$–$C_6$ isomerization. The first feedstock and the second feedstock enter the process via lines 16 and 18, respectively, while a stream of make-up hydrogen enters the process through line 20. Both feedstocks and the make-up hydrogen pass respectively through a drier 17, 19 and 21 before entering the isomerization zones. The driers preferably contain an adsorbent material with a type 4A molecular sieve being particularly preferred for the hydrogen and $C_5$–$C_6$ feedstock and a type 13X molecular sieve being particularly preferred for the $C_4$ feedstock. However, any type of drier that will meet the limitations for moisture as hereinafter discussed can be used for the feedstocks and hydrogen.

The feedstock carried by line 16 is admixed with make-up hydrogen from line 20 to form a first combined feedstream. Line 22 carries the first combined feedstream through an exchanger 24 to heat the incoming feed against the effluent of the isomerization zone 10 carried by a line 29. Final heating of the combined feedstream takes place in a charge heater 26 that exchanges the feedstream against medium pressure steam. After final heating, the first combined feedstream enters a single reactor 28 that contains a hereinafter described preferred catalyst composition. The effluent from reactor 28 comprising a $C_4$ isomerate product stream is taken from the reactor 28 by line 29, cooled in a charge heater 30 and exchanger 24 before entering separation section 14.

Following passage through drier 19, line 18 carries the second feedstock into admixture with a stream of recycled hydrogen carried by line 32 to form a second combined feedstream transported by line 34. Line 34 conducts the second combined feedstream through a series of exchangers 36, 38 and charge heater 30. Isomerization zone 12 includes a first reactor 40 and a second reactor 42; both reactors 40 and 42 contain a preferred catalyst composition as hereinafter feedstream may also contain low concentrations of unsaturated hydrocarbons and hydrocarbons having more than 6 carbon atoms. The concentration of these materials should be limited to 10 wt. % for unsaturated compounds and 20 wt. % for heavier hydrocarbons in order to restrict hydrogen consumption and cracking reactions. The feed may also contain substantial quantities of naphthenic hydrocarbons, the concentration of these components should not normally exceed 35 mol %.

Hydrogen is admixed with each feed in an amount that will provide a hydrogen to hydrocarbon ratio equal to or less than 1.0 at the inlet of the isomerization zone. The hydrogen to hydrocarbon ratio of 1 or less has been found to provide sufficient excess hydrogen for operation of the isomerization zones. Although no net hydrogen is consumed in the isomerization reactions, the isomerization zones usually have a net consumption of hydrogen often referred to as the stoichiometric hydrogen requirement which is associated with a number of side reactions that occur. These side reactions include cracking and disproportionation. Other reactions that will also consume hydrogen include olefin and aromatics saturation. High hydrogen concentrations tend to inhibit the isomerization of butanes by reducing the partial pressure of butane in the vapor phase and thus reducing the rate of reaction, therefore, high hydrogen to hydrocarbon ratios in the $C_4$ isomerization zone should be avoided. In general, a preferred hydrogen to hydrocarbon ratio is between 0.05 to 0.5.

Hydrogen may be added to the feed mixture in any manner that provides the necessary control for the addition of small hydrogen quantities. Metering and monitoring devices for this purpose are well known by those skilled in the art. As currently practiced, a control valve is used to meter the addition of hydrogen to the feed mixture. The hydrogen concentration in one or both of the effluent streams or one of the outlet stream fractions can be monitored by a hydrogen monitor and the control valve positions adjusted to maintain the desired hydrogen concentration.

The hydrogen and hydrocarbon feed mixture entering either isomerization zone is contacted in at least one reaction zone with an isomerization catalyst. This invention can be practiced using a variety of different catalyst compositions and is not limited to a particular catalyst or combination of catalysts for either isomerization zone. A preferred isomerization catalyst consists of a high chloride catalyst on an alumina base containing platinum. In which case the alumina is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will typically contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process.

The preferred catalyst also contains a chloride component. The chloride component termed in the art "a combined chloride" is present in an amount from about 2 to about 10 wt. % based upon the dry support material. The use of chloride in amounts greater than 4 wt. % have been found to be the most beneficial for this process.

There are a variety of ways for preparing the preferred catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the halogen. Halogen may also be added to the carrier material by contacting the calcined carrier material with an aqueous solution of the halogen acid such as hydrogen chloride, hydrogen fluoride, or hydrogen bromide.

It is generally known that high chlorided platinum-alumina catalysts of this type are highly sensitive to sulfur and oxygen-containing compounds. Therefore, the feedstocks and any make-up hydrogen entering the process must be relatively free of such compounds when the preferred catalyst is used. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. The feedstock and hydrogen stream may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

Operation of the isomerization zones with the preferred catalyst also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, methylenechloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

Operating conditions within the isomerization zones are selected to provide a good selectivity of the particular isoalkane product from the feed components. The core of the operation of the $C_4$ isomerization zone is passage of the $C_4$ feedstock through a reactor at butane isomerization-promoting conditions including the presence of an acidic isomerization catalyst. This is normally a relatively low pressure operation performed at a pressure of from about 700 to 4000 kPag and at an elevated temperature as required by the activity of the catalyst. The average reactant temperature may be as high as 500° C., but is preferably between 100° and 320° C. It is preferred that the $C_4$ feedstock is passed vertically through one or more fixed beds of catalyst located within the reactor at a liquid hourly space velocity between 2.0 and 100, but space velocities in the broad range of 0.5 to 12.0 can be employed if desired.

The $C_5$-$C_6$ isomerization zone will operate at conditions to maximize the isomerization of $C_5$ and $C_6$ hydrocarbons. Thus, temperatures within the reaction zone will range from about 90°-225° C. (194°-435° F.). Lower reaction temperatures in this range favor equilibrium mixtures of $C_5$ and $C_6$ isoalkanes versus normal pentane and hexane. However, higher temperatures in the range of 200°-225° C. (390°-435° F.) are preferred when large quantities of normal butanes are in the combined feed to the $C_5$-$C_6$ isomerization zone. The higher temperatures offer a significant increase in isobutane production with only a minimal decrease in the ratio of $C_5$ and $C_6$ isoalkanes to pentane and hexane. Of course, the most suitable temperature will depend on the composition of the feed. For feeds having few isomerizable $C_4$ hydrocarbons, temperatures of between 120°-205° C. (248°-400° F.) may be most advantageous. The $C_5$-$C_6$ isomerization zone may also be maintained over a wide range of pressures. Pressure conditions in the isomerization of $C_5$-$C_6$ paraffins range from 700 to 7000 kPag. Preferred pressures for this isomerization are in the range of from 2000 to 3000 kPag. The feed rate to this reaction zone can also vary over a wide range and includes liquid hourly space velocities ranging from 0.5 to 10 hr.$^{-1}$, however, space velocities between 0.5 and 4 hr.$^{-1}$ are preferred.

The $C_5$-$C_6$ isomerization zone will usually contain multiple stages. A typical $C_5$-$C_6$ isomerization zone will have a two-reactor system comprising a first stage reactor and a second stage reactor. The catalyst used in a multiple reaction stage system is usually distributed equally between the different reaction stages. It is not necessary that either reaction zone be carried out in two or more reactors but the use of at least two reactors confers several benefits on the process. The use of two reactors and specialized valving (not shown) allows partial replacement of the catalyst in the system without taking the subject isomerization zone off stream. For the short periods of time during which replacement of catalyst may be necessary, the entire flow of reactants may be processed through only one reaction vessel while catalyst is replaced in the other. Two reactors can also be used to maintain lower catalyst temperatures in a portion of the $C_5$-$C_6$ isomerization zone. This is accomplished by having any exothermic reaction such as hydrogenation of unsaturates performed in a first reaction vessel with the rest of the reaction carried out in a final reactor stage at lower temperature conditions. Therefore, the first reactor can operate at a somewhat higher temperature, of about 200°-225° C., (390°-435° F.) which favors the isomerization of butanes and the lower temperature of the second reactor will increase the $C_5$ and $C_6$ isoparaffin to paraffins ratios by a small amount without reversing the isobutane yield. When two reactors are used in this manner, the last reactor in the $C_5$-$C_6$ isomerization zone can be operated at a temperature below 190° C. (375° F.) and possibly as low as 150° C. (302° F.).

Operation of the C₄ isomerization zone at a relatively higher temperature than that the C₅–C₆ isomerization zone and the operation of reactor 40 at a relatively higher operating temperature than reactor 42 allows the process arrangement of this invention to take advantage of a beneficial heat integration. As shown in FIG. 1, the second combined feed is first progressively heated by indirect heat exchange with the effluent from reactors 42 and 40. After the initial heat exchange, the C₄ isomerate product carried by line 29 has enough heat, in most cases, to raise the temperature of the second combined feedstream to the desired inlet temperature for reactor 40. Of course, heat from line 29 may be supplemented, if necessary, by an additional charge heater if a higher inlet temperature is desired for reactor 40. As hereinafter described, heat from the C₄ isomerate product may be transferred to the second combined feedstream by indirect heat exchange, direct contact, or a combination thereof.

The effluents from both isomerization zones are combined following any heat exchange. FIG. 1 shows the isomerate products carried by lines 29 and 46 combined into a common product stream 48 that enters separation facilities for recovering the isomerization product. At minimum, the separation facilities divide the reaction zone effluent into a product stream comprising C₄ and heavier hydrocarbons and a gas stream which is made up of lighter hydrocarbons and hydrogen. Suitable designs for rectification columns and separator vessels are well known to those skilled in the art. The separation section may also include facilities for recovery of normal alkanes. Normal alkanes recovered from the separation facilities may be recycled to the isomerization reaction zone to increase the conversion of normal alkanes to isoalkanes. One typical arrangement for the separation facilities is shown in FIG. 1 and includes an overhead condensor 50 that cools the combined isomerate products and a product separator 52 that receives the cooled effluent from condensor 50 via line 48. Product separator 52 recovers hydrogen and other light gases in recycle stream 54 and directs unstabilized liquid products to a stabilizer column 56 by a line 58. Hydrogen from line 54 is compressed in a recycle compressor 55 for recycle to the C₅–C₆ isomerization zone by line 32. The stabilizer 56 column is operated to deliver a bottoms fraction 60 containing C₄ and heavier hydrocarbons and an overhead fraction 62 of C₃ hydrocarbons and lighter boiling compounds. Products taken from the bottom of the column can be cooled with the combined product stream in heat exchanger 64 before it enters the column. C₃ and lighter hydrocarbons taken overhead from stabilizer column 56 can be cooled and separated into a gas stream and reflux that returns to the separation column.

When the preferred catalyst is used, net gas from the separator column will ordinarily enter a scrubber section 66 that contacts the gas with a suitable treatment solution for neutralizing and/or removing acidic components that may have originated with the chloride addition to the isomerization zone and may be present in the gas stream. Typically, the treatment solution will be a caustic that is pumped in a loop around a contacting vessel. After treatment in the scrubber section, the net gas is removed from the process by line 63 and usually put to use as a fuel.

In most isomerization processes and as depicted by FIG. 1, hydrogen is separated from the effluent in a product recovery section and recycled to the isomerization zone. When the hydrogen to hydrocarbon ratio of the reactor effluent is less than 0.05, it is possible to separate light ends from an isomerization effluent without the recovery and recyle of hydrogen to either of the isomerization zones. As the quantity of hydrogen leaving the product recovery section increases, additional amounts of C₄ and other product hydrocarbons are taken with the light ends that are separated from the process. These product hydrocarbons are typically in the fuel gas stream from the product recovery section. The value of the lost product or the additional expense associated with recovery facilities to prevent the loss of product do not normally justify operating the process without recycle at effluent hydrogen to hydrocarbon ratios above 0.05.

Figure 2:
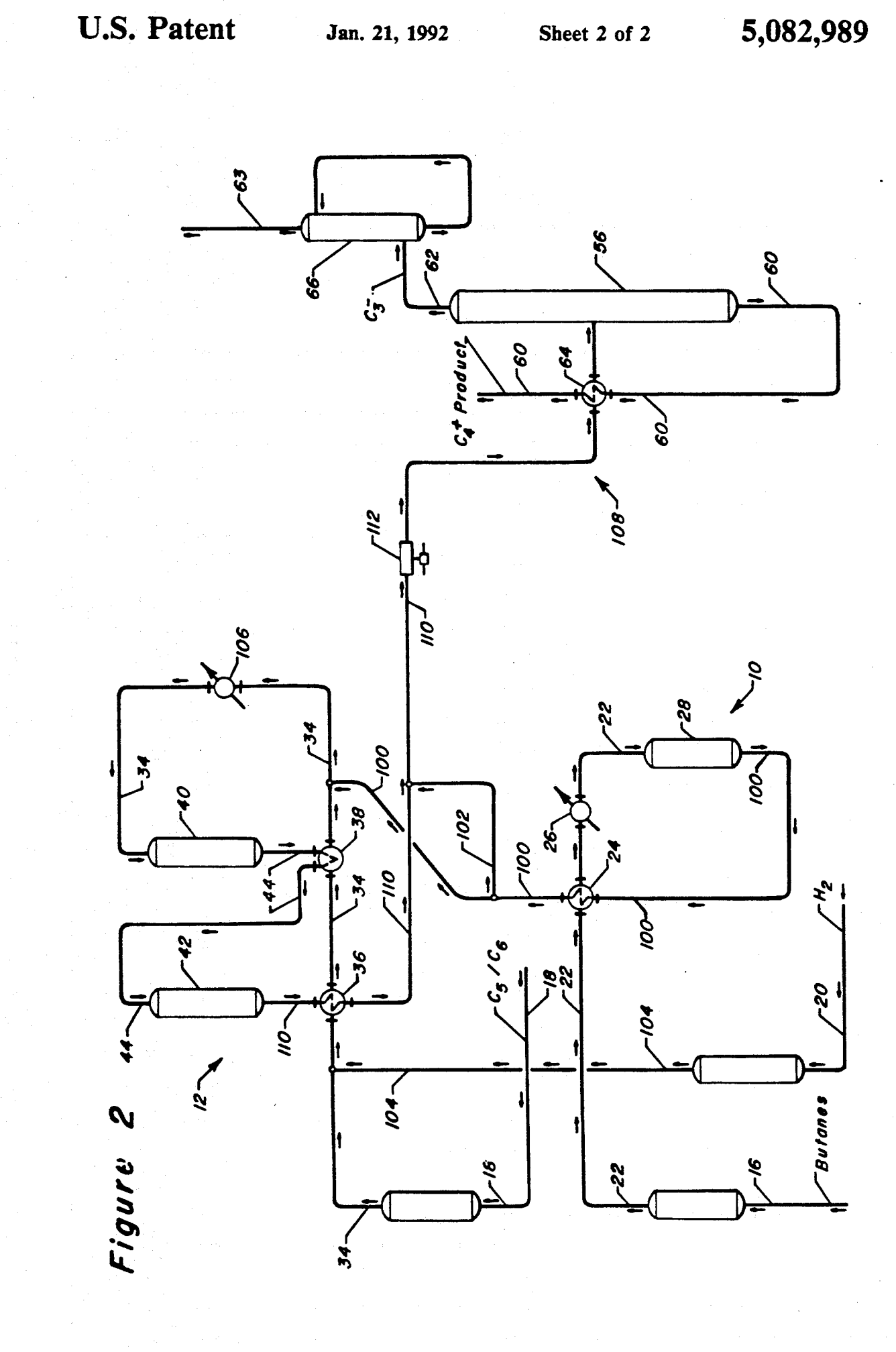

In another embodiment of this process, as illustrated by FIG. 2, isomerate product from the C₄ isomerization zone directly contacts the isomerate product from the C₅–C₆ isomerization zone and the separation facilities operate without the recycle of hydrogen. The process arrangement of FIG. 2 still contains isomerization zones 10 and 12 and as described in conjunction with FIG. 1 as well as separation facilities. This arrangement simplifies the process arrangement of FIG. 1 by eliminating the product separator 52, the recycle compressor 55 and the heater 30 as shown in FIG. 1.

Looking then at FIG. 2, the C₄ feedstock again enters the process via line 16 and after drying in drier 17 is combined with the dried hydrogen stream from line 20. The amount of hydrogen combined with the C₄ feed may vary and at a minimum will equal the minimum amount of hydrogen necessary for the operation of the C₄ isomerization zone and at a maximum will equal enough hydrogen to supply the hydrogen requirements of both isomerization zones. The first combined feedstream is taken by line 22 and passed through the first isomerization zone in the manner previously stated for the description of FIG. 1. The effluent from reactor 28 is taken by line 100 and passed through exchanger 24 to heat the incoming feed.

Depending on the flow capacity of the reactors in the C₅–C₆ isomerization zone, all or a portion of the isomerate product from the C₄ isomerization zone is mixed directly with the second combined feedstream carried by line 34 to provide a mixed feedstream carried by line 34'. It is preferable to combine all of the isomerate product from line 100 directly with the second combined feedstream since this allows all of the required hydrogen for the C₅–C₆ isomerization zone to be transferred directly to the second feedstock and all of the available heat in line 100 to be utilized. Any flow capacity limitation will stem from space velocity limitations in the reactors of isomerization zone 12. If the C₅–C₆ isomerization zone has insufficient flow capacity for all of the effluent carried by line 100, a portion of the line 100 effluent is diverted into the effluent from the C₅–C₆ isomerization zone by line 102. If the flow through line 102 is large, a heater similar to heater 30 shown in FIG. 1 can be provided to heat the second feedstock against line 102. Thus in a further embodiment of this invention the effluent from the C₄ isomerization can be split between line 100 and line 102, and the split regulated to control the space velocity in isomerization zone 12, the amount of hydrogen added to the second feedstock via line 100 and the amount of direct heating obtained from line 100.

When all of the hydrogen requirements for isomerization zone 12 cannot be supplied by the effluent from isomerization zone 10, a portion of the hydrogen for the C$_5$-C$_6$ isomerization zone is supplied by diverting a portion of hydrogen stream from line 20 into line 104. Even when all of the effluent from isomerization zone 10 is combined with the C$_5$-C$_6$ feedstock, it may still be desirable to supply a portion of the hydrogen requirements for isomerization zone 12 through line 104 in order to lower the hydrogen partial pressure in isomerization zone 10.

FIG. 2 also shows the addition of a charge heater 106 for supplying additional heat to the mixed feedstream carried by line 34'. The use of the charge heater provides additional flexibility to the process by making up for any heat lost by the diversion of the C$_4$ isomerate through line 102. Except as otherwise described, the reactors and effluent heat exchange for isomerization zone 12 are essentially the same as that described in conjunction with FIG. 1.

All of the effluent from both isomerization zones is eventually combined and together enters a separation facility 108 via line 110. The combined effluent is carried by line 110 through a condensor 112 and directly into a stabilizer column. Since in this embodiment both isomerization zones operate with a minimum hydrogen to hydrocarbon ratio, there is no need for a product separator to recover hydrogen for recycle to the isomerization zones. Apart from a slightly higher hydrogen concentration in the stabilizer overhead stream, the operation of the stabilizer section for the embodiment of FIG. 2 parallel that of FIG. 1.

I claim:

1. A process for isomerizing a first feedstock comprising normal butane and a second feedstock comprising C$_5$ and C$_6$ acyclic hydrocarbons, said process comprising:
    a) combining said first feedstock with a portion of a hydrogen stream to produce a first combined feedstream comprising hydrogen and normal butane;
    b) passing said first combined feedstream to a first isomerization zone and contacting said first combined feedstream, at butane isomerization conditions, with an isomerization catalyst and withdrawing a first isomerization zone effluent comprising isobutane and hydrogen from said first isomerization zone;
    c) heating said second feedstock by at least indirectly contacting said first isomerization zone effluent with said second feedstock and admixing at least a portion of the hydrogen from said hydrogen stream with said second feedstock to produce a second combined feedstream;
    d) passing said second combined feedstream to a second isomerization zone and contacting said second combined feedstream with an isomerization catalyst at conditions for the isomerization of C$_5$ and C$_6$ hydrocarbons and withdrawing a second isomerization zone effluent;
    e) passing said first and second effluent streams to a common separation zone;
    f) withdrawing a first light gas stream comprising hydrogen from said separation zone; and
    g) withdrawing at least one product stream comprising branched-chain hydrocarbons from said separation zone.

2. The process of claim 1 wherein said portion of hydrogen for admixing with said second feedstock is recovered from said separation zone.

3. The process of claim 1 wherein at least a portion of said first effluent stream is mixed with said second feedstock to effect said contacting and supply, at least in part, said portion of said hydrogen from said hydrogen stream.

4. The process of claim 1 wherein a second portion of said hydrogen stream is admixed with said second feedstock.

5. The process of claim 1 wherein the isomerization conditions in said first isomerization zone include LHSV in a range of from 2 to 10, a temperature in a range of from 100° to 300° C. and a pressure in a range of from 700 to 4000 kpag, and the isomerization conditions in said second isomerization zone include an LHSV in a range of from 0.5 to 4, a temperature in a range of from 90° C. to 225° C., and a pressure in a range of from 2000 to 3000 kPag.

6. The process of claim 1 wherein said first feedstock is admixed with hydrogen in an amount that will produce a hydrogen to hydrocarbon ratio of less than 0.5 in and said first effluent stream and said second feedstock is admixed with hydrogen in an amount that will produce a hydrogen to hydrocarbon ratio of less than 0.05 in said second effluent.

7. The process of claim 1 wherein said separation zone recovers essentially all of the hydrogen from said first and second effluent streams in a light gas stream comprising C$_3$ and lower boiling materials and said light gas stream is withdrawn from the process.

8. The process of claim 1 wherein the isomerization catalyst in said first and second isomerization zones comprises alumina, 0.01 to 0.25 wt. % platinum and from 2 to 10 wt. % of a chloride component.

9. A process for isomerizing a first feedstock comprising normal butane and a second feedstock comprising C$_5$ and C$_6$ acyclic hydrocarbons, said process comprising:
    a) combining said first feedstock with a least a portion of a hydrogen stream to produce a first combined feedstream comprising hydrogen and normal butane;
    b) passing said first combined feedstream to said first isomerization zone and contacting said first combined feedstream, at butane isomerization conditions, with an isomerization catalyst comprising alumina, 0.01 to 0.25 wt. % platinum and from 2 to 10 wt. % of a chloride component and withdrawing a first isomerization zone effluent comprising isobutane and hydrogen;
    c) mixing at least a portion of said first isomerization zone effluent with said second feedstock to produce a second combined feedstream and maintaining a hydrogen concentration in said second combined feedstream that will produce a hydrogen to hydrocarbon mol ratio in a second effluent stream from a second isomerization zone that is less than 0.05;
    d) passing said second combined feedstream to said second isomerization zone and contacting said second combined feedstream with an isomerization catalyst comprising alumina, 0.01 to 0.25 wt. % platinum and from 2 to 10 wt. % of a chloride component at conditions for the isomerization of C$_5$ and C$_6$ hydrocarbons, said conditions including a temperature that is lower than the temperature in said first isomerization zone, and withdrawing a second isomerization zone effluent having a hydrogen to hydrocarbon ratio of less than 0.05 from said second isomerization zone;

e) passing said second effluent stream to a separation zone;

f) withdrawing a first light gas stream from said separation zone containing essentially all of the hydrogen entering said separation zone and removing said light gas stream from said process; and g) withdrawing at least one product stream comprising branched-chain hydrocarbons from said separation zone.

10. The process of claim 9 wherein all of said first isomerization zone effluent is passed directly to and combined with said second isomerization zone effluent.

11. The process of claim 10 wherein a portion of said hydrogen stream is mixed directly with said second feedstock.

12. The process of claim 11 wherein the isomerization conditions in said first isomerization zone include an LHSV in a range of from 2 to 10, a temperature in a range of from 100° to 300° C. and a pressure in a range of from 700 to 4000 kPag, and the isomerization conditions in said second isomerization zone include an LHSV in a range of from 0.5 to 4, a temperature in a range of from 90° C. to 225° C., and a pressure in a range of from 2000 to 3000 kPag.

13. The process of claim 12 wherein said first feedstock is admixed with hydrogen in an amount that will produce a hydrogen to hydrocarbon ratio of less than 0.5 in said first effluent stream and said second feedstock is admixed with hydrogen in an amount that will produce a hydrogen to hydrocarbon ratio of less than 0.05 in said second effluent.

* * * * *